United States Patent [19]

Couillard

[11] Patent Number: 4,597,866
[45] Date of Patent: Jul. 1, 1986

[54] CHROMATOGRAPHY APPARATUS

[75] Inventor: François Couillard, Serres Castet, France

[73] Assignee: Groupe Industriel de Realisations et Applications, Morlaas, France

[21] Appl. No.: 675,337

[22] Filed: Nov. 27, 1984

[30] Foreign Application Priority Data

Dec. 2, 1983 [FR] France .............................. 83 19315
Nov. 22, 1984 [FR] France .............................. 84 17796

[51] Int. Cl.⁴ .............................................. B01D 15/08
[52] U.S. Cl. .................................. 210/198.2; 210/352
[58] Field of Search .................. 210/198.2, 236, 350, 210/351, 352

[56] References Cited

U.S. PATENT DOCUMENTS

| | | | |
|---|---|---|---|
| 3,511,377 | 12/1970 | Hrdina .............................. | 210/198.2 |
| 3,966,609 | 6/1976 | Godbille et al. .................. | 210/198.2 |
| 3,997,446 | 12/1976 | Nagakura ............................. | 210/350 |
| 4,093,548 | 6/1978 | Sterkenburg et al. .............. | 210/350 |
| 4,347,137 | 8/1982 | Dick, Jr. ............................. | 210/350 |

*Primary Examiner*—John Adee
*Attorney, Agent, or Firm*—Burgess, Ryan & Wayne

[57] ABSTRACT

In a chromatographic column assembly comprising a tubular column a first end of which is sealed, the second end of said column is also sealed in order to form an enclosure between said second end and a piston. A pressurized fluid introduced into this enclosure displaces the piston in the direction corresponding to compression of a packing or filling provided in the column. A flexible conduit ensures the circulation of a fluid to be chromatographed and crosses through the piston, the enclosure containing the pressurized fluid and the second end of the column.

12 Claims, 8 Drawing Figures

CHROMATOGRAPHY APPARATUS

BACKGROUND OF THE INVENTION

The present invention concerns improvements to chromatography apparatus and in particular to columns containing a porous packing.

It is known in the prior art to utilize tubular columns presenting a piston or other sliding body to ram or compress the packing in a chamber between this piston and a fixed bottom or detachable cover; the piston being displaced by a jack or other actuating device associated with the piston rod.

The present invention is aimed at facilitating the operations concerned and simplifying the material required for their achievement in order to ensure improved conditions during the successive steps involved, which comprise filling the column with the packing, compressing the same, the chromatography properly speaking, while maintaining the compression and, furthermore, the final phase consisting either in returning to initial conditions, or in emptying the column especially with a view to changing the packing.

French patent No. 72 07278 discloses chromatography apparatus constituted by a column intended to contain a support made of adsorbing material, the column comprising:

a tube provided at one of its ends with a fluid-permeable (i.e. permeable to liquids or gases) cover and communicating with the outside;

a body sliding along the axis of the tube and consisting of a piston formed, on the one hand, of a head constituted by a porous plate which is permeable to fluids and which exerts to exert a pressure inside the tube, and, on the other hand, a piston rod controlling the displacement of the piston head.

This French patent indicated that the apparatus so disclosed exerts a pressure on the particles intended to constitute the adsorbent support. Such a pressure can be exerted during the filling of the column, after a suspension of particles of the material has been introduced into the tube, in order to thus cause the liquid to pass through the porous plates and to compress the particles between the sliding body and the cover, and thus to form the adsorbent support necessary for exactly operating the chromatography process, namely to prevent poor homogeneity of the packing which constitutes a serious defect in the chromatography columns.

In fact the apparatus described in this French patent presents several drawbacks:

In the one hand, it requires a piston rod in order to transmit to the piston head the displacement necessary to ensure the expulsion of the liquid forming the suspension of the particles of which the packing is formed. This rod must have a length at least equal to the length of travel or stroke of the piston and thus requires a length that is practically equal to the length of the column, if it is desired to utilize the column only on a small portion of its total length. Indeed, such a stroke of the piston (which would be in certain cases about 3 to 4 meters) requires below the column a space sufficient to ensure this stroke;

on the other hand, when, following extended use of a column, a slight compression of the packing occurs in the column due to contraction, crushing or weak dilution of the adsorbent mass leading to a loss of resolution power of the column, it is no longer possible to compensate such undesirable compression if the piston stroke is limited to one portion of the column, so that it is necessary to open the column and add a further amount of adsorbent material; this is not simple to do and can become necessary rather often, not to mention the fact that in the case of thin packings smaller than the size of the adsorbent mass particles, this can prove to be impossible.

The present invention concerns an improved apparatus allowing to overcome the drawbacks of the known apparatus and especially of the apparatus according to the above-mentioned French patent.

In fact, the chromatography apparatus according to the invention can be utilized with widely variable volumes of adsorbent mass without requiring the availability of a large lost volume below or above the column in order to ensure the piston stroke. Furthermore, the novel apparatus does not require heavy investment in equipment having different dimensions, since a single column of considerable length can be adapted to any length required. Furthermore, the problems of sealing and maintaining this sealing are easier to overcome.

The present invention provides an improved chromatography apparatus or column constituted by a tube, one portion of which constitutes a chamber intended to contain a packing or adsorbent material mass, this tube comprising at each of its ends an end wall presenting communicating means for communication with the outside and, on the other hand, at last one sliding body being longitudinally displacible within the cylinder and having connecting means for connection with a duct communicating with the outside, wherein the sliding body is displaced by the pressure exerted by a pressurized fluid injected into an enclosure formed between the sliding body and the end wall opposite facing the chamber containing the packing.

Furthermore, the means provided to produce the pressure in the enclosure include a hydraulic circuit comprising, on the one hand, a conduit connecting said enclosure to an elution agent reservoir and the portion of the tube intended to contain the packing, the conduit associated to a pump and a first valve, the circuit also comprising, on the other hand, a shunting conduit possibly comprising a second valve, and connecting the enclosure to the input conduit at a point located between the pump and the first valve.

Two calibrated flap valves are also provided, respectively positioned on the input conduit between the point and the first valve, and on the shunting conduits between the point and the enclosure.

Furthermore, the shunting conduit comprises between the enclosure and the flap valve an evacuation conduit for the hydraulic fluid, which conduit comprises a third valve. The sliding body or piston is crossed through, by connecting means consisting of a conduit communicating with the atmosphere, this conduit being a flexible conduit the length of which is at least equal to the possible stroke of the sliding body.

Two sliding bodies can also be provided, each of them being disposed at a respective one of the ends of the above-mentioned tube, a connection being established between the two enclosures.

Other various arrangements can be envisaged, and in particular, the following:

The surface of the sliding body intended to be opposed to the packing is larger than the surface of the sliding body intended to be in contact with the packing.

The sliding body comprises means of connection with the means for communicating with the atmosphere which are provided in the end wall, these communicating means being connected to a supply circuit of the flowable phase intended to be used for the elution.

The pressure intended to be exerted in the enclosure is produced by means of the elution fluid and the additional pressure results from the relative calibration clearances of the calibrated flap valves placed on the hydraulic circuit and the shunting conduit.

In order to cause the piston or sliding body to be returned after the chromatography step proper, it is possible to reverse the flow direction of the fluid between the pump and the enclosure utilized for the propulsion by a set of valves and reversal channels.

In order to prevent the packing particles from tending to be introduced between the piston and the tubular column, the fluid is brought to the piston and enters the chromatography chamber by inlets disposed along the periphery of the piston, whereby the particles tend to spread out from the wall of the tube immediately adjacent to the piston.

The piston can also comprise a device sealing these inlets during the chromatography step proper, for example, beyond a selected pressure threshold.

When two pistons having two sections are provided, these may be constituted by two elements able to be repaired when one of them reaches at the end of the stroke, so as to modify the pressure exerted on the packing. Therefore, by limiting the stroke of the large-diameter portion, the pressure is only exerted on a smaller section or area during the chromatography step. It is also possible to utilize pistons double-acting or simultaneously and/or successively acting pistons. It can be envisaged, too not to use simple sealing caps or covers for enclosing the column, but heads containing the pistons and their supply conduits, which considerably simplifies assembly and disassembly.

Another object of the present invention is to provide a chromatographic separation process consisting essentially in positioning the packing, of exerting the fluid pressure in order to compress the same, continuing to exert a pressure necessary for maintaining the compression during the chromatography step proper, carrying out the elution step, then possibly in modifying the pressure either to return to the initial conditions, or with a view to changing the packing.

BRIEF DESCRIPTION OF THE DRAWINGS

In order to better understand the technical features and advantages of the present invention, various embodiments will now be described, by way of non-limitative example, with reference to the appended drawings in which.

In all the examples, reference will be made to the chromatography in liquid phase, by way of illustration, which those skilled in the art will easily transpose onto chromatography in supercritical or gaseous phase without departing from the spirit and scope of the invention.

Figure 1:
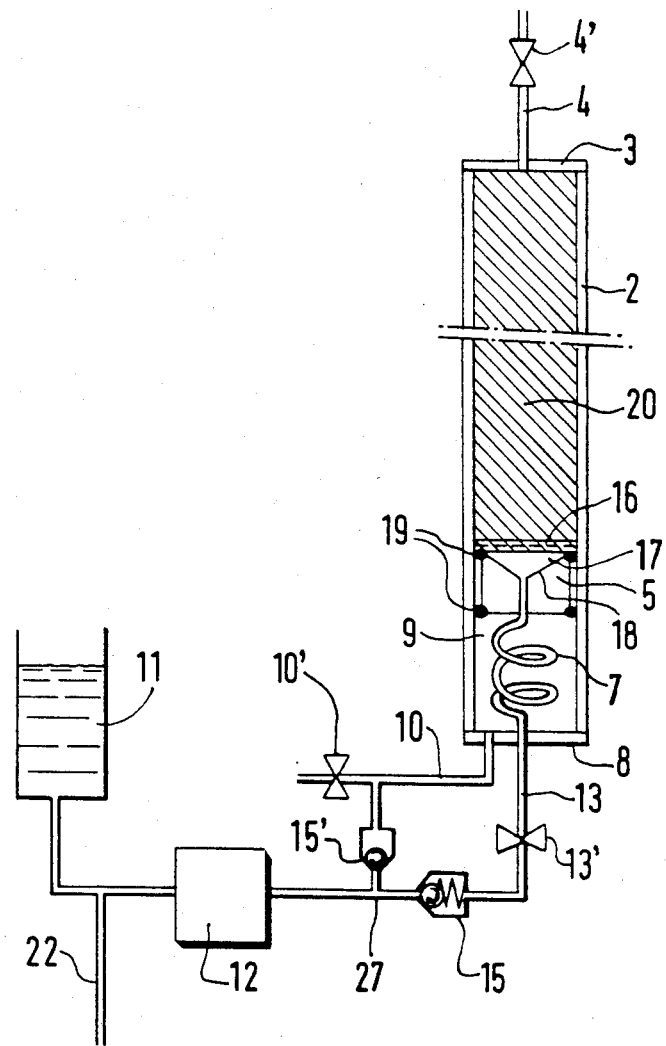
FIGS. 1 to 6 are axial sectional views of six different embodiments of chromatographic devices according to the invention, FIG. 6 being limited to the section of the head of the column.

FIG. 1 represents the liquid phase chromatograph column and the elements associated therewith.

FIG. 1 is a diagrammatic representation of a chromatography apparatus comprising a tube 2 a portion of which is adapted to contain a packing or absorbing mass 20, an end wall, in the present case a cover 3 having communicating means 4 for communication with outside the column and a valve 4'. Tube 2 comprises a body or piston 5 sliding longitudinally in tube 2 and having connecting means for connection with a conduit 7, such means consisting of a flexible tube communicating with the atmosphere. Between the sliding body or piston 5 and the bottom 8 of the column an enclosure 9 is formed into which opens a shunting conduit 10 for a hydraulic fluid connected to a tank or reservoir 11 and supplied by a pump 12. An evacuation or outlet valve 10' and a calibrated flap valve 15' are placed on the conduit 10. Flexible tube 7, the length of which is at least equal to the possible stroke of the sliding body (thus practically equal to the length of tube 2) opens into a conduit 13 comprising a valve 13' and a calibrated flap valve 15. Conduits 13 and 10 are connected to each other at a point 27 downstream from pump 12 with respect to the fluid flow direction.

The connecting means are constituted by porous pressure-resistant plates 16 and a conduit 17 the upper portion of which has the shape of a funnel 18. Sealing means 19 consisting of annular joints such as 0-rings and/or lips, are disposed between the tube and sliding body 5 and are preferably carried by piston-shaped body 5.

The chromatography device according to FIG. 1 operates as follows:

Cover 3 being removed, a suspension of adsorbent particles such as a silicon gel in a liquid, for example, is poured into tube 2. Cover 3 is refitted in place and fixed so as to provide a sealed closure. Thereafter the sliding body is displaced by starting pump 12 and injecting hydraulic fluid (in this case the elution agent) into enclosure 9 through conduit 10 under a pressure sufficient to cause the sliding body to be displaced upwardly and to exert a pressure on the suspension present in the tube 2 and thus to force the liquid through conduit 4 and to evacuate it through this conduit.

When the liquid of the suspension has been totally evacuated, valve 13' is opened and the pressure exerted by pump 12 is maintained at a working pressure higher than the pressure which is to prevail in the chromatography column during operation.

The mixture to be chromatographed will be introduced through conduit 13 and calibrated stop valve 15, valve 13' being opened, and, after treatment, will leave the treatment zone through conduit 4, while the mixture passes through the valve 13' and the flap valve 15' into enclosure 9.

By way of non-limitative example, operating parameters of the column are given herein-below:

(a) step of filling-in the adsorbent mass

This step corresponds to the compression phase.

The pressure exerted by the pump is 10 bars. When the liquid of the suspension has been completely evacuated through conduit 4 and the mass has been suitably compressed, the chromatography step is carried out.

(b) chromatography step

The pressure generated by supply pump 12 feeding the mixture to be chromatographed is 53 bars.

After passage through the calibrated stop valve 15 at 13 bars, this pressure falls to 40 bars, which is the pressure corresponding to the pressure loss in the column.

In shunting conduit 10, due to the fact that flap valve 15' is calibrated at 3 bars, the pressure after passage of this flap valve is of 50 bars the counter pressure which is exerted on sliding body 5 in enclosure 9 and which is opposed to the pressure prevailing in column 2.

It will be observed that the active portion of tube 2, i.e. that portion which contains packing 20 and in which chromatography is intended to be carried out can have any determined volume.

Furthermore, if it is desired to drain enclosure 9, it is sufficient to open valve 10'.

The embodiment of FIG. 1 is of great economic interest since, furthermore, in order to displace sliding body 5 and maintain the compression of the adsorbent mass, the pressure generated by the pump supplying the mixture to be chromatographed and the eluant is utilized. Sealing problems are, furthermore, overcome, since the enclosure and the portion of the tube containing packing 20 contain the same mixture.

Furthermore, in the case where at the end of a relatively long period of operation of the device decreased compression of the adsorbent mass becomes evident (due to dilution of a small proportion of the particles, clogging or any other reason), it is possible to compensate such insufficient compression by correspondingly displacing sliding body 5.

Sliding body 5 in the embodiment of FIG. 1 is shown to be located in the lower part of the column. It could, of course, be placed in the upper part, or again the column may comprise two sliding bodies situated each at one of the ends of the column, a connection being established between the sliding body placed at the top of the column and the wall of the corresponding end or, more generally, a connection being established between the two enclosures thus created (cf. description of FIG. 5 herein-under).

Figure 2:
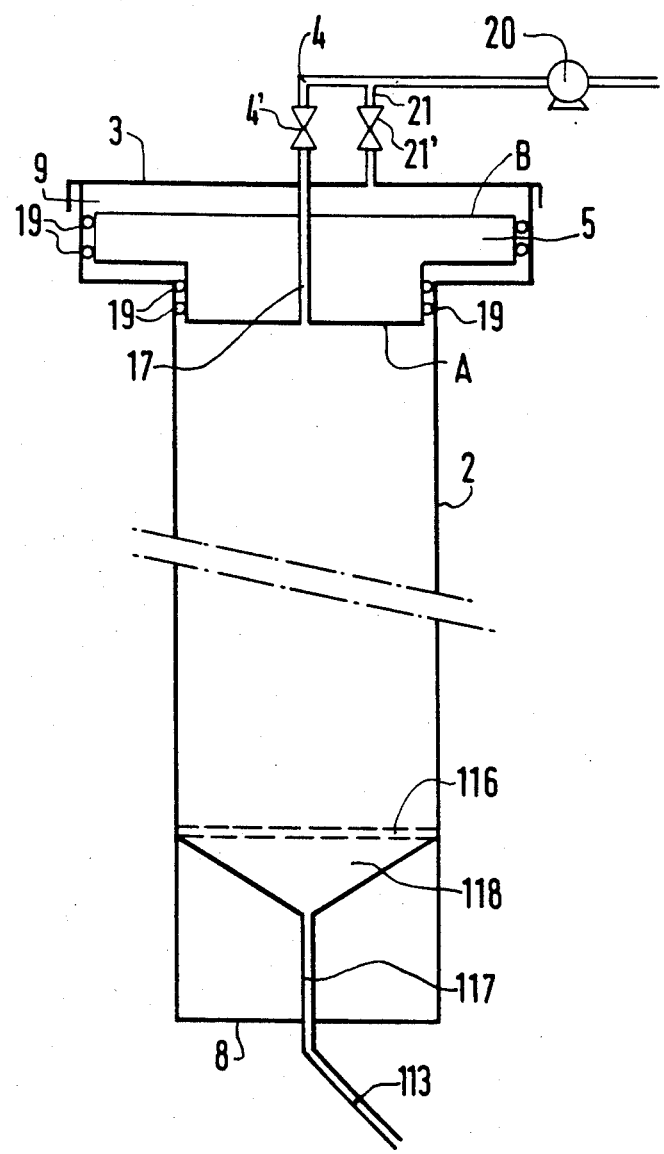

FIG. 2 represents a second embodiment of the chromatography device of the invention, especially intended to compensate the packing down that can be produced in the adsorbent mass.

The chromatography device shown in this figure comprises a certain number of references identical to those of FIG. 1, which correspond to similar elements. The elements bearing the same references preceded by the number 1 correspond to those elements having the same functions, even though they may be of a different construction.

A pump 20 is disposed on tube 4, which is provided with a by-pass 21 and a valve 21'. Sliding body 5 comprises a face B, on the side of enclosure 9 and a face A on the side of the adsorbent material the area of face B being larger than that of face A. Thus the force exerted on face A is smaller than that exerted on face B.

The mixture to be chromatographed and/or the eluant can be supplied through conduit 4 and after purification can be evacuated through conduits 117 and 113.

Part of the mixture can be derived by conduit 21, the valve 21' being open, and can thus enter enclosure 9. Due to the difference between the areas of faces B and A of sliding body 5, the force exerted on B is greater than the force exerted on A and this means that any deficiency of compression of the adsorbent mass is compensated progressively as it occurs.

The supply pressure of pump 20, i.e. 120 bars, is equal to the pressure intended to prevail in the column.

It may be noted by way of example, that in practice, the surface of face A being 85 cm$^2$ and the surface of face B being 87.5 cm$^2$, this will result in a pressure of 10 bars exerted on the packing.

Figure 3:
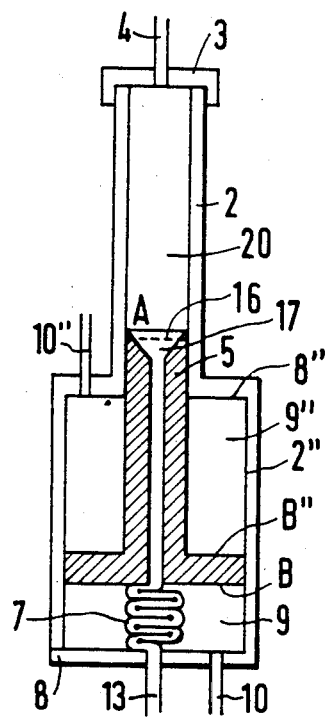

It is obvious that the solution of FIG. 2 allows also to overcome easily the problem of the pressure requirements according to which the pressure forces acting to displace the piston should be greater than the pressure forces acting in the opposite direction, which are exerted by the fluid in the chromatography chamber. In the case of FIG. 1, where the piston has equal diameters, it is necessary that the pressure in enclosure 9 be greater than that in pump 20. In the case of FIG. 2, the unitary pressure can be the same on A and on B, provided that the surface of B is greater than that of A. Now, as it has already been stressed, if it is desired that the piston has a stroke of sufficient length, this involves a proportional increase of the height of the column. If this increase of height is not troublesome (premises with high ceilings or small experimental chromatography apparatus) it is possible to utilize devices of the type shown in FIG. 3. FIG. 3 represents elements designated by the same reference numerals as the similar elements of FIGS. 1 and 2.

The large-diameter piston portion B leaves a space 9" between its face B" and the shoulder 8" that separates the portion of the tube 2 and 2" having different respective diameters. The stroke of the piston is limited by this shoulder 8" against which face B" of the large-diameter piston portion abuts.

Figure 4:
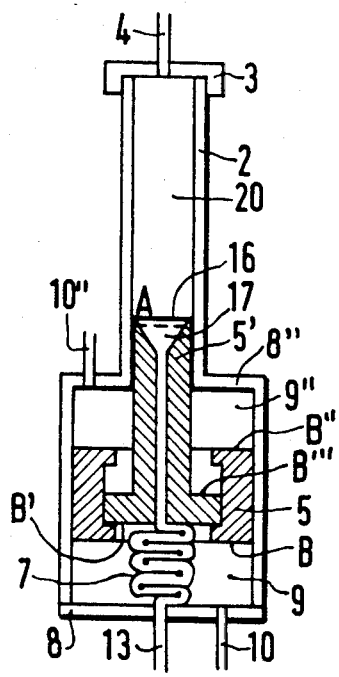

Once the filling has been conveniently compressed (and the liquid expelled from the gel, for example), the pressure necessary for maintaining the compression can be weaker in pump 20; it is possible to operate thereafter with reduced pressure forces. It is then possible to utilize solutions of the type represented in FIG. 4. In this case, when the large diameter face B" of the piston abuts at 8", portion 5' of the piston continues to advance, the pressure in enclosure 9 only being exerted on the intermediary section B' of the piston that is displaced in the internal boring of the large-diameter portion of the piston. This results in reducing the forces exerted on B' and 5' and consequently the forces necessary to maintain the compression of the packing.

Figure 5:
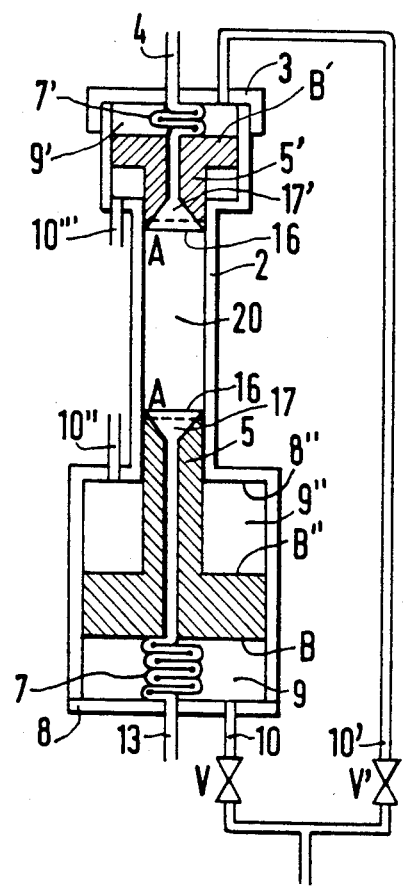

As shown in FIG. 5, it is also possible to combine a lower piston for compressing the packing down with an upper piston for maintaining the compression during the chromatography steps. The situation is thus similar to that described herein-above where enclosures 9 and 9' are supplied through conduits 10 and 10' from the same source and can furthermore be made to communicate again by opening valves V and V'.

Indeed, in the case where the lower piston abuts (B in 8") the upper piston becomes active. If the dimensional parameters are suitably chosen, the lower piston can ensure the compressing and the upper piston can adequately maintain the compression during the chromatography step proper.

It will be noted that, as in all the other cases where the filling is performed in the easiest way by introducing the packing material through the top, it is necessary to remove cap 3 and lower piston 5. The area of B being larger than that of B', itself superior to A', the lower piston is the one that moves forward during the compression phase. When B" abuts at 8", piston 5 is stationary and piston 5' advances, thus maintaining the compression with a reduced force (moreover the weight of the piston 5' can be involved in this action of maintaining the compression).

Figure 6:
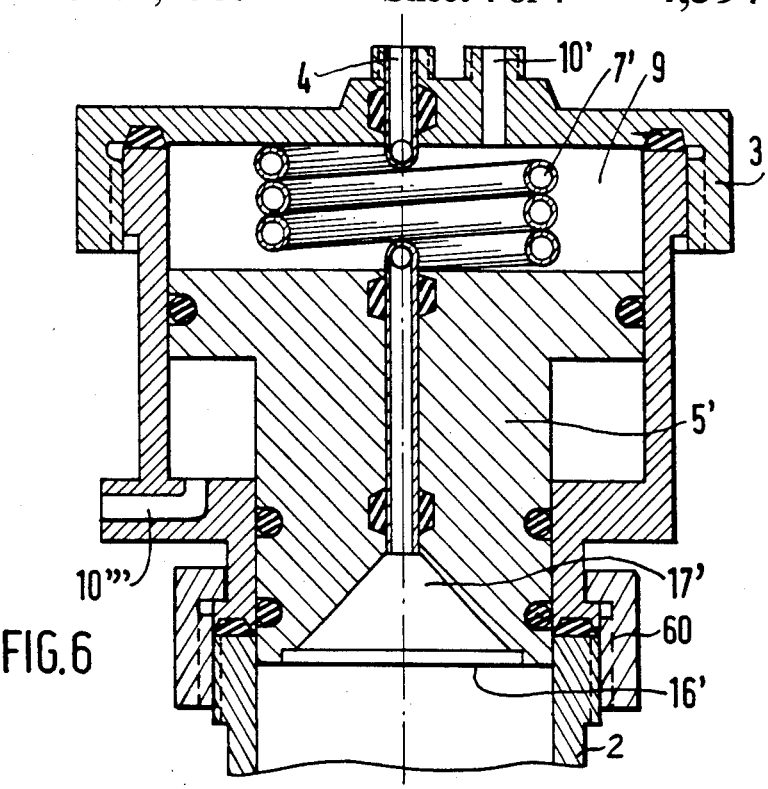

FIG. 6 represents a dismountable column head assembly in its entirety, i.e. with its piston. Assembling means such as a ring 60 allows the assembly to be placed on the tubular column 2. This applies to the upper piston as well as to the lower piston, the tubular portion of the column being reduced to a plain cylindrical tube. Such a device provides for great flexibility of assembly (one or two pistons having different diameters, etc...).

Figure 7:
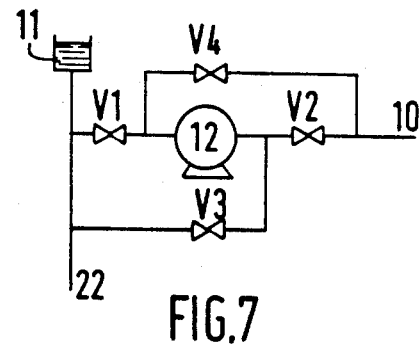
FIG. 7 shows a mounting circuit of a pump for fluid reversal flow.

If it is required to return at least partially to the initial state, after the achievement of the chromatography step it is necessary to bring back the pistons. Two solutions are possible: applying the pressure in 10"(FIGS. 3, 4, 5) and 10'''(FIG. 6) or, in the absence of 10" and 10''' generating a depletion of fluid by means of 10 (FIGS. 2, 4, 5) and 10' (FIG. 6). To this end, it is sufficient to invert the mounting of the pump, for example, by means of the device of FIG. 7 or an equivalent equipment, a set of valves and conduits or channels ensuring the reversal.

When V1 and V2 are open, V3 and V4 being closed, the fluid flows in one direction, for example, from left to right in the pump, and, flows-counter-wise when V1 and V2 are closed and V3 and V4 are open. The other references of FIG. 7 correspond to those used in FIG. 1.

As to the structure of the pistons, reference will be made to FIG. 8.

Any piston or other sliding body is provided with sealing means such as seals, joints or segments, so that the particulate packing tends to penetrate the clearance or interval exisiting between the piston and the wall of the tubular column.

It is obvious that this can lead to logging and wear, as well as to leaking resulting therefrom.

It is therefore desireable to remove to any extent possible the particles of the packing of the zone adjacent to the periphery of the piston. For this purpose, during the moving forward of the piston, i.e. during the compressing operations, the liquid is not introduced through the central portion of the piston, but through openings disposed along the periphery, these openings being closed during the chromatography step. This assignment can be applied to all the pistons of FIGS. 1 to 6.

Piston 5 mounted in tube 2 is constituted by a hollow body 50 formed by a bottom wall and a peripheral wall 52. This peripheral wall is provided with grooves containing joints 53 or segments or other sealing elements. Inside the body, a movable element 54 is disposed, which has the general form of a funnel 17 (same reference as in the preceding figures) and which is constituted by an assembly of a grid and a material 16 pervious to the fluid but impervious to the packing particles which deposit on its upper face. This element 54 is placed on a spring 55 which normally holds it at a distance from body 50 and provides between the respective peripheries of the two components a port 56. The fluid arriving through 13 can thus flow towards chamber 20 by passing through this peripheral port 56. When piston 5 is performing the compression operation and when the pressure becomes sufficient to compress spring 55, the element 54 sinks into body 50 and the ports are closed. Openings 57 provided in the bottom of the funnel 54 are placed opposite facing holes 58 of a cylinder 69 integral with the bottom, which makes the funnel accessible to the fluid arriving through 13. When the spring is calibrated in accordance with the pressure prevailing at the end of the compression phase, the components connected will automatically pass from one position to the other. When the fluid arrives in 56, it prevents the packing particles from entering the clearance between the piston and the tube, which allows incidents during the forward motion of the piston to be prevented. When the fluid arrives through the funnel, it is ready for the chromatographic operation properly speaking.

Figure 8:
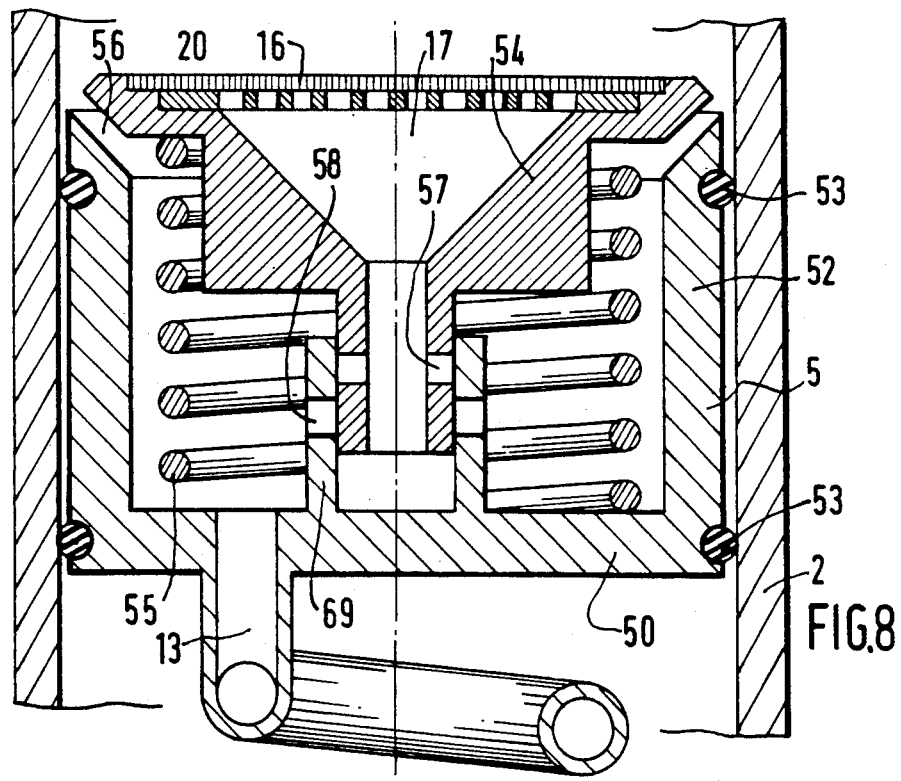
FIG. 8 is a realization detail of an axial sectional view of one embodiment of a piston.

It is obvious that the embodiments shown in the figures are given only by way of non-limitative illustration and that, for example, with respect to FIG. 8 other systems can produce the same effects by using equivalent means. Those skilled in the art will be able to envisage various modifications to the apparatus and the operating conditions. It should, furthermore, be noted that in order to simplify the present description the construction and operating details that are evident for those skilled in the art have been omitted.

It is well understood that the present invention is not limited to the embodiments described herein-above and shown in the appended drawing, but can be adapted to numerous variants available to those skilled in the art, without departing from the scope and spirit of the invention.

What is claimed is:

1. A chromatographic column assembly comprising: a tubular column having first and second sealed ends, a sealed piston slidable within the column for compressing a filling placed in a tubular chamber defined between the piston and said first sealed end of the tubular column,
communicating means provided in the piston and in said first sealed end for ensuring a circulation of fluid to be chromatographed through the filling,
a sealed enclosure defined between said piston and said second sealed end and independent of the circulation of the fluid to be chromatographed, and which contains a pressurized fluid which displaces said piston in the direction of said filling, and a flexible conduit ensuring the independent circulation of the fluid to be chromatographed and crossing through the second sealed end of said column, the enclosure containing the pressurized fluid and said piston.

2. An assembly according to claim 1, wherein said column is provided with two pistons between which is formed the tubular chamber receiving the filling.

3. An assembly according to claim 2, wherein one of said pistons is displaced by pressurized fluid introduced into an enclosed defined between said piston and a corresponding column end, a second flexible conduit being mounted in the same manner as said one flexible conduit to the other piston.

4. An assembly according to claim 1, wherein the pressurized fluid is constituted by one of an eluant and the fluid to be chromatographed.

5. An assembly according to claim 1, wherein to ensure the compression of said filling, the pressure of the pressurized fluid is higher in said enclosure than in the tubular chamber.

6. An assembly according to claim 1, wherein said piston has two sections with different respective diameters and sliding in corresponding bores of said assembly, the small diameter section being located on the side of the enclosure receiving the pressurized fluid.

7. An assembly according to claim 6, wherein the pressure of the pressurized fluid is equal to the pressure prevailing in the tubular chamber in order to ensure compression of said filling.

8. An assembly according to claim 6, wherein a space defined between the location of the connection of the two sections of the boring which have different respective diameters and the large diameter section of the piston communicates with the pressurized fluid in order to ensure the return of the piston.

9. An assembly according to claim 1, further comprising a circuit supplying the enclosure with pressurized fluid, said circuit being provided with a reversal device to ensure return of the piston.

10. An assembly according to claim 1, wherein one end of the column includes a movable head containing the piston, fluid supply means and means to control the piston motions.

11. An assembly according to claim 1, wherein the fluid to be chromatographed arriving in said piston is introduced into the tubular chamber through peripheral openings of the piston face which faces the filling.

12. An assembly according to claim 11, wherein said openings are sealed during the chromatography step, the fluid thus flowing through a funnel which is open towards the filling and provided in the piston, and which is sealed on the side of the filling by pressure resistant means which are permeable to fluid but impermeable to the filling.

* * * * *